United States Patent [19]

Schommer et al.

[11] Patent Number: 4,950,763

[45] Date of Patent: Aug. 21, 1990

[54] PREPARATION OF KETONES

[75] Inventors: Charles Schommer, Ludwigshafen; Klaus Ebel, Mutterstadt; Toni Dockner, Meckenheim; Matthias Irgang, Heidelberg; Wolfgang Hoelderich, Frankenthal; Harald Rust, Neustadt-Duttweiler, all of Fed. Rep. of Germany

[73] Assignee: BASF Aktiengesellschaft, Ludwigshafen, Fed. Rep. of Germany

[21] Appl. No.: 381,469

[22] Filed: Jul. 18, 1989

[30] Foreign Application Priority Data

Jul. 29, 1988 [DE] Fed. Rep. of Germany ....... 3825873
Jun. 21, 1989 [DE] Fed. Rep. of Germany ....... 3920280

[51] Int. Cl.$^5$ ............................................. C07C 45/48
[52] U.S. Cl. ..................................... 546/314; 568/314; 568/319; 568/346; 568/354; 568/388; 568/397
[58] Field of Search ............... 568/317, 354, 319, 388, 568/314, 346

[56] References Cited

U.S. PATENT DOCUMENTS

| 4,528,400 | 7/1985 | Cryberg et al. | 568/314 |
| 4,570,021 | 2/1986 | Cryberg et al. | 568/388 |

FOREIGN PATENT DOCUMENTS

| 85996 | 8/1983 | European Pat. Off. | 568/397 |
| 283660 | 9/1988 | European Pat. Off. | 568/397 |
| 2111722 | 4/1974 | Fed. Rep. of Germany | 568/397 |
| 2758113 | 1/1981 | Fed. Rep. of Germany | 568/397 |
| 1090287 | 11/1967 | United Kingdom | 568/397 |

OTHER PUBLICATIONS

Takeda, Chem. Abst., vol. 103, #8004v (1985).
Criado et al., Chem. Abst., vol. 91, #73890d (1979).
Takeda, Chem. Abst., vol. 102, #138494w (1985).
Houben/Weyl, Methoden der Organischen Chemie, vol. VII/2a, pp. 627–633 (1973).

*Primary Examiner*—James H. Reamer
*Attorney, Agent, or Firm*—John H. Shurtleff

[57] ABSTRACT

Ketones of the general formula (I)

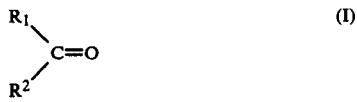

where $R^1$ and $R^2$ independently of one another are each alkyl, cycyloalkyl, arylalkyl, aryl or hetaryl, and one or more of the radicals $R^1$ and $R^2$ carry one or more hydrogen atoms on the α-carbon atom, are prepared by reacting two carboxylic acids of the general formulae (IIa/IIb), $R^1$—COOH (IIa) and $R^2$—COOH (IIb) or by reacting a carboxylic acid $R^1$—COOH (IIa) and a ketone

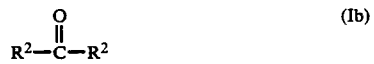

or by reacting a mixture of IIa, IIb and Ib, in the gas phase in the presence of a catalyst, by a process in which a catalyst is used whose active material contains at least 50% by weight of titanium dioxide having a specific surface area greater than 10 m$^2$/g.0.

12 Claims, No Drawings

PREPARATION OF KETONES

The present invention relates to a novel and improved process for the preparation of ketones by gas-phase decarboxylation of a carboxylic acid or a mixture of a carboxylic acid and a ketone, with dehydration, over a catalyst which contain titanium dioxide and whose specific surface area is not less than 10 m$^2$/g.

Houben-Weyl, Methoden der organischen Chemie, Volume VII/2a, page 627–633, 1973, discloses that, instead of carboxylic acids, it is also possible to use their derivatives, for example carboxylic esters, nitriles and anhydrides. This is of particular interest when the carboxylic acids are sparingly volatile or tend to undergo decarboxylation during vaporization.

It is generally known (for example from DE-A-21 11 722) that, inter alia, catalysts containing zirconium dioxide or thorium dioxide, particularly those having alumina as a carrier, can be used for this reaction. The yields achievable with these catalysts and the duration of activity of the said catalysts were not completely satisfactory.

DE-A-27 58 113 discloses catalysts which consist of zirconium dioxide or thorium dioxide on anatase as a carrier. Although these have better long-term activity compared with the abovementioned ones, they too are not completely satisfactory.

Furthermore, JP 58/13537, US-A-4,528,400 and US-A-4,570,021 disclose the heterogeneously catalyzed reaction of pivalic acid with either acetone or acetic acid (EP-A-85 996) in the gas phase over ZrO$_2$, CeO$_2$/Al$_2$O$_3$ and ThO$_2$/Al$_2$O$_3$. The catalysts which may be used are expensive and/or radioactive and the yields are unsatisfactory.

It is an object of the present invention to overcome the disadvantages of the known processes.

We have found that this object is achieved by a novel and improved process for the preparation of ketones of the general formula (I)

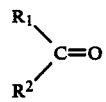

where R$^1$ and R$^2$ independently of one another are each alkyl, cycloalkyl, aralkyl, aryl or hetaryl, and one or more of the radicals R$^1$ and R$^2$ carry one or more, ie. one, two or three, hydrogen atoms on the α-carbon atom, by reacting two carboxylic acids of the general formulae (IIa/IIb), R$^1$-COOH (IIa) and R$^2$-COOH (IIb) or by reacting a carboxylic acid R$^1$-COOH (IIa) and a ketone

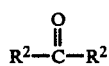

or by reacting a mixture of IIa, IIb and Ib, in the gas phase in the presence of a catalyst, wherein the catalyst used is one whose active material contains at least 50% by weight of titanium dioxide having a specific surface area greater than 10 m$^2$/g. The active material of the catalyst contains from 50 to 100, preferably from 50 to 99.95,% by weight of titanium dioxide of said surface area.

If R$^1$ is identical to R$^2$, the ketones are symmetric ketones; in asymmetric ketones, on the other hand, R$^1$ and R$^2$ are different. If R$^1$ and R$^2$ together form a biradical, the relevant reaction is the reaction of a dicarboxylic acid to form a cyclic ketone. However, it is also possible to react a dicarboxylic acid with two or more equivalents of a monocarboxylic acid to give a diketone.

The selectivity with respect to the desired ketones is particularly high if the specific surface area is greater than 10, preferably from 20 to 200, m$^2$/g and if the catalyst contains from 0.05 to 50, preferably from 1 to 10,% by weight of one or more metal oxides selected from the first or second main group of the Periodic Table, in particular from the elements lithium, sodium and potassium, or from the group consisting of the rare earth metals, in particular from the elements lanthanum and cerium. The titanium dioxide is advantageously used in the form of anatase.

The novel catalysts can be used in the form of impregnated or mixed catalysts.

Preparation of impregnated catalysts

The starting material used is titanium dioxide having a large surface area, for example pyrogenic TiO$_2$ or dried metatitanic acid, which is brought into a moldable state with the addition of peptizing agents in a kneader or mixer. The kneaded material is extruded and the extrudates are dried and calcined. The porosity is determined, after which an impregnating solution whose volume corresponds to the pore capacity of the carrier is used.

Impregnation is effected by adding the impregnating solution to the initially taken carrier in a rotating drum, advantageously by spraying the said solution onto the said carrier. The impregnating solutions can be prepared using any soluble salts which decompose to oxides on calcination, without leaving further residues.

Preparation of mixed catalysts

The mixed catalysts are prepared in a manner similar to that used for the carriers of the impregnated catalysts. The corresponding salt solutions are also added to the TiO$_2$ material in the kneader and thorough mixing is ensured. Molding, drying and calcination are carried out as for the preparation of the carriers.

The catalysts can be regenerated by heating in air or in an air/nitrogen mixture at from 450 to 550° C.

The spent catalyst can simply be recycled to the sulfuric acid digestion.

The novel process gives ketones or mixtures of ketones

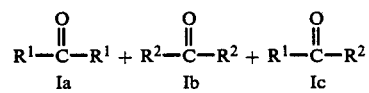

with decarboxylation and dehydration.

In the preparation of mixed ketones Ic, the statistical ratio of Ia to Ib to Ic of 0.25 : 0.25 : 0.50 is not normally reached. Because of the different activities of the starting acids, the more active acid preferentially reacts with itself, and only a small amount of this acid is available for formation of the mixed ketone. When acetic acid and isobutyric acid were used, for example, only 45% of the desired methyl isopropyl ketone were obtained by the known processes. A substantial advantage of the novel catalysts is the fact that the less reactive acids too are more strongly activated than in the case of conventional catalysts, so that the differences in activity are smaller. Accordingly, the yield of methyl isopropyl ketone in the process of the invention is 71%, based on converted isobutyric acid, with quantitative conversion.

If the mixture used contains a carboxylic acid without α-hydrogen atoms $R^1$—COOH, ie. a carboxylic acid with a tertiary α-carbon atom, such as pivalic acid or an aromatic carboxylic acid (a substituted benzoic acid), only two ketones Ib and Ic are obtained since $R^1$—COOH does not undergo autocondensation. In this case, the novel catalysts give yields of up to 99% of the desired aymmetric ketone (eg. propiophenone).

The yield of mixed ketone can also be increased if the more active acid is used in up to a 10-fold molar excess compared with the less active acid; in this case, however, correspondingly large amounts of the symmetric ketone of the excess acid are obtained.

In the preparation of asymmetric ketones Ic, the carboxylic acid $R^2$—COOH (IIb) used as the educt may also be replaced by the symmetric ketone $R^2$—CO—$R^2$—(Ib) obtained therefrom in the reaction, which then likewise reacts to give the desired ketone Ic according to the following equation:

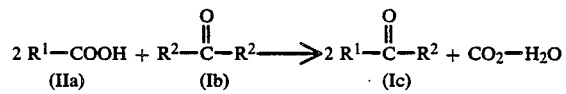

In addition, mixtures of carboxylic acid IIb and ketone Ib may be reacted with the carboxylic acid IIa to give I, and excess ketone Ib may then be recycled to the reaction after distillation. This variation can be used ketones, eg. pinacolone, methyl isopropyl ketone and acetophenones, the methyl component which is reacted with, for example, pivalic acid, isobutyric acid or an aromatic carboxylic acid being in this case acetic acid, acetone or a mixture thereof.

$R^1$ and $R^2$ are each preferably alkyl of 1 to 17 carbon atoms, cycloalkyl having 3 to 8 ring members, arylalkyl of 7 to 12 carbon atoms, aryl or hetaryl, and one or more of the radicals $R^1$ and $R^2$ carry one or more hydrogen atoms on the α-carbon atom.

Examples of important ketones which are used as solvents or intermediates for the preparation of dyes, crop protection agents, drugs and vitamins and which are also obtainable by the novel process from the corresponding acids are diethyl ketone, di-n-propyl ketone, diisopropyl ketone, methyl propyl ketone, methyl isopropyl ketone, ethyl isopropyl ketone, nonan-5-one, octane-2,7-dione, cyclopentanone, cycloheptanone, acetophenone, propiophenone, butyrophenone, isobutyrophenone, valerophenone, phenylacetone, 1,2-diphenylacetone, cyclohexyl methyl ketone, cyclohexyl phenyl ketone, cyclopropyl methyl ketone, pinacolone and even heterocyclic ketones, such as 3-acetylpyridine, 4-acetylpyrazole and 4-acetylimidazole.

It is possible to use carboxylic acids which contain up to 50% by weight of water, and since the water frequently has an advantageous effect on the active life of the catalysts (less carbon is deposited on the catalyst) it is often even advantageous to add from 1 to 50% by weight of water to the carboxylic acids.

The decarboxylation reaction with dehydration is preferably carried out under atmospheric pressure and at from 300 to 600° C., especially from 350 to 450° C., by passing the acid vapors, preheated to this temperature, through a fixed-bed oven which is filled with catalyst extrudates, granules, pellets, chips or rings, or by carrying out the reaction in a fluidized-bed oven. In the case of sparingly volatile acids, it may also be advisable to employ reduced pressure. In general, from 200 to 500 g/h of ketones can be prepared per liter of catalyst.

After passing the catalyst zone, the vapors are cooled and are worked up in a conventional manner. In general, conversions of from 97 to 100% and ketone yields, based on these conversions, of from 55 to 85% in the case of asymmetric ketones and from 90 to 99% in the case of symmetric ketones are obtained.

EXAMPLE 1

Preparation of catalysts

Titanium dioxide having a surface area of about 120 $m^2/g$ is used for the preparation of the catalysts, the said titanium dioxide being kneaded with the addition of water and 3% (based on titanium dioxide) of nitric acid and then extruded, and the extrudates being dried and calcined. The extrudates thus obtained have a porosity of about 0.5 ml/g and a BET surface area of about 100 $m^2/g$. The porosity of the carrier is determined exactly. The extrudates are impregnated with impregnating solutions in a rotating drum until the pores have been filled.

1.1 A solution which contains 13 g of $Na_2O$ (as aqueous NaOH) is sprayed onto 987 g of $TiO_2$ carrier.
1.2 A solution which contains 25 g of $K_2O$ (as aqueous KOH) is sprayed onto 975 g of $TiO_2$ carrier.
1.3 A solution which contains 100 g of $CeO_2$ (as aqueous cerium nitrate solution) is sprayed onto 900 g of $TiO_2$ carrier.

The impregnated catalysts are dried at 120° C. for 16 hours and calcined at 500° C. for 1 hour.

EXAMPLE 2

Preparation of diethyl ketone

A mixture of 44 g/h of propionic acid and 6g/h of water was evaporated in an evaporator and passed, together with 3 l/h of nitrogen, at 360° C., over 100 ml of a catalyst which contained 2% by weight of potassium oxide, the remainder being anatase. The reaction gases were then cooled and were collected in a receiver. From the discharged two-phase mixture, the organic phase was analyzed by gas chromatography. The conversion of propionic acid was 100%. The selectivity with respect to diethyl ketone was 99%.

EXAMPLE 3

Preparation of methyl isopropyl ketone

A mixture of 32 g/h of isobutyric acid, 32 g/h of acetic acid and 16 g/h of water was evaporated in an evaporator and passed, together with 3 l/h of nitrogen, at 420° C., over 170 ml of a catalyst which contained 1.3% by weight of sodium oxide, the remainder being anatase. The reaction gases were then cooled and were collected in a receiver. From the discharged two-phase mixture, the organic phase was analyzed by gas chromatography. The conversion of isobutyric acid was 100.0%. The selectivity with respect to methyl isopropyl ketone was 72.0%.

EXAMPLE 4

Preparation of pinacolone

A mixture of 15 g/h of pivalic acid, 52 g/h of acetic acid and 17 g/h of water was evaporated in an evaporator and passed, together with 3 l/h of nitrogen, at 450° C., over 100 ml of a catalyst which contained 1.3% by weight of sodium oxide, the remainder being anatase. The reaction gases were then cooled and were collected in a receiver. From the discharged two-phase mixture, the organic phase was analyzed by gas chromatography. The conversion of pivalic acid was 99%. The selectivity with respect to pinacolone was 81%.

EXAMPLE 5

Preparation of propiophenone

A mixture of 16 g/h of benzoic acid, 57 g/h of propionic acid and 14.5 g/h of water was evaporated in an evaporator and passed, together with 10 l/h of nitrogen, at 400° C., over 100 ml of a catalyst which contained 2.5% by weight of sodium oxide, the remainder being anatase. The reaction gases were then cooled and were collected in a receiver. From the discharged two-phase mixture, the organic phase was analyzed by gas chromatography. The conversion of both carboxylic acids was 100%. The selectivity with respect to propiophenone was 99%.

EXAMPLE 6

Preparation of cyclohexyl phenyl ketone

A mixture of 11.5 g/h of benzoic acid, 36 g/h of cyclohexanecarboxylic acid and 13 g/h of water was evaporated in an evaporator and passed, together with 10 l/h of nitrogen, at 450° C., over 100 ml of a catalyst which contained 2% by weight of potassium oxide, the remainder being anatase. The reaction gases were then cooled and were collected in a receiver. From the discharged two-phase mixture, the organic phase was analyzed by gas chromatography. The conversion of benzoic acid was 98%. The selectivity with respect to cyclohexyl phenyl ketone was 60%.

EXAMPLE 7

Preparation of 3-acetylpyridine

A mixture of 29 g/h of methyl nicotinate, 76 g/h of acetic acid and 26 g/h of water was evaporated in an evaporator and passed, together with 10 l/h of nitrogen, at 420° C., over 150 ml of a catalyst which contained 2% by weight of sodium oxide, the remainder being anatase. The reaction gases were then cooled and were collected in a receiver. From the discharged two-phase mixture, the organic phase was analyzed by gas chromatography. The conversion of nicotinic ester and of acetic acid was 100% in each case. The selectivity with respect to 3-acetylpyridine was 54%. In addition, pyridine was formed with a selectivity of 41%.

EXAMPLE 8

Preparation of further catalysts

Catalyst carrier I

Titanium dioxide having a surface area of 120 m²/g was used, the said titanium dioxide being kneaded with the addition of water and 3% (based on titanium dioxide) of nitric acid and then extruded, and the extrudates being dried and calcined.

Catalyst carrier II

Titanium dioxide having a surface area of about 40 m²/g was used, the said titanium dioxide being kneaded with the addition of water, 4% (based on titanium dioxide) of potato starch, 5% of ammonia water (25% of $NH_3$) and then extruded, and the extrudates being dried and calcined.

The extrudates thus obtained are impregnated with impregnating solutions in a rotating drum until the pores have been filled.

| Catalyst | Carrier [g] | Additive [g] | Aqueous solution of | Examples |
|---|---|---|---|---|
| A | II 980 | $K_2O$ 20 | KOH | 2 |
| B | I 987 | $Na_2O$ 13 | NaOH | 3,4 |
| C | I 975 | $Na_2O$ 25 | NaOH | 5 |
| D | I 980 | $K_2O$ 20 | KOH | 6 |
| E | I 980 | $Na_2O$ 20 | NaOH | 7,13 |
| F | II 980 | $Li_2O$ 20 | LiOH | 9 |
| G | II 980 | $Na_2O$ 20 | NaOH | 10 |
| H | II 980 | $Rb_2O$ 20 | $Rb_2CO_3$ | 11 |
| J | II 980 | $Cs_2O$ 20 | $Cs_2CO_3$ | 12 |
| K | II 995 | $Na_2O$ 5 | NaOH | 14 |
| L | I 997 | $Na_2O$ 3 | NaOH | 15 |
| M | II 999 | $K_2O$ 1 | KOH | 16 |
| N | II 997 | $Na_2O$ 3 | NaOH | 17 |

EXAMPLE 9

Preparation of diethyl ketone

A mixture of 43 g/h of propionic acid and 5 g/h of water was evaporated in an evaporator and passed, together with 3 l/h of nitrogen, at 360° C., over 100 ml of catalyst F, which contained 2% by weight of lithium oxide, the remainder being anatase. The catalyst was prepared similarly to Example 8, by impregnating 980 g of $TiO_2$ carrier II with a solution which contained 20 g of $Li_2O$ (as aqueous LiOH). The reaction gases were then cooled and were collected in a receiver. From the discharged two-phase mixture, the organic phase was analyzed by gas chromatography. The conversion of propionic acid was 100%. The selectivity with respect to diethyl ketone was 95%.

EXAMPLE 10

Preparation of diethyl ketone

A mixture of 53 g/h of propionic acid and 7 g/h of water was evaporated in an evaporator and passed, together with 3 l/h of nitrogen, at 360° C., over 100 ml of catalyst G, which contained 2% by weight of sodium oxide, the remainder being anatase. The catalyst was prepared similarly to Example 8, by impregnating 980 g of $TiO_2$ carrier II with a solution which contained 20 g of $Na_2O$ (as aqueous NaOH). The reaction gases were then cooled and were collected in a receiver. From the discharged two-phase mixture, the organic phase was analyzed by gas chromatography. The conversion of propionic acid was 99%. The selectivity with respect to diethyl ketone was 99%.

EXAMPLE 11

Preparation of diethyl ketone

A mixture of 53 g/h of propionic acid and 7 g/h of water was evaporated in an evaporator and passed, together with 3 l/h of nitrogen, at 360° C., over 100 ml of catalyst H, which contained 2% by weight of rubidium oxide, the remainder being anatase. The catalyst was prepared similarly to Example 8, by impregnating 980 g of $TiO_2$ carrier II with a solution which contained 20 g of $Rb_2O$ (as aqueous $Rb_2CO_3$). The reaction gases were then cooled and were collected in a receiver. From the discharged two-phase mixture, the organic phase was analyzed by gas chromatography. The conversion of propionic acid was 100%. The selectivity with respect to diethyl ketone was 98%.

EXAMPLE 12

Preparation of diethyl ketone

A mixture of 43 g/h of propionic acid and 5 g/h of water was evaporated in an evaporator and passed, together with 3 l/h of nitrogen, at 360° C., over 100 ml of catalyst J, which contained 2% by weight of cesium oxide, the remainder being anatase. The catalyst was prepared similarly to Example 8, by impregnating 980 g of $TiO_2$ carrier II with a solution which contained 20 g of $Cs_2O$ (as aqueous $Cs_2CO_3$). The reaction gases were then cooled and were collected in a receiver. From the discharged two-phase mixture, the organic phase was analyzed by gas chromatography. The conversion of propionic acid was 100%. The selectivity with respect to diethyl ketone was 97%.

EXAMPLE 13

Preparation of 3-acetylpyridine

A mixture of 22 g/h of methyl nicotinate, 57 g/h of acetic acid and 20 g/h of water was evaporated in an evaporator and passed, together with 10 l/h of nitrogen, at 400° C., over 100 ml of catalyst E, which contained 2% by weight of sodium oxide, the remainder being anatase. The catalyst was prepared similarly to Example 8, by impregnating 980 g of $TiO_2$ carrier I with a solution which contained 20 g of $Na_2O$ (as aqueous NaOH). The reaction gases were then cooled and were collected in a receiver. From the discharged two-phase mixture, the organic phase was analyzed by gas chromatography. The conversion of nicotinic ester and of acetic acid was 100% in each case. The selectivity with respect to 3-acetylpyridine was 60%. In addition, pyridine was formed with a selectivity of 29%.

EXAMPLE 14

Preparation of pinacolone

A mixture of 15 g/h of pivalic acid, 52 g/h of acetic acid and 13 g/h of water was evaporated in an evaporator and passed, together with 3 l/h of nitrogen, at 415° C., over 100 ml of catalyst K, which contained 0.5% by weight of sodium oxide, the remainder being anatase. The catalyst was prepared similarly to Example 8, by impregnating 995 g of $TiO_2$ carrier II with a solution which contained 5 g of $Na_2O$ (as aqueous NaOH). The reaction gases were then cooled and were collected in a receiver. From the discharged two-phase mixture, the organic and the aqueous phase were analyzed by gas chromatography. The conversion of pivalic acid was 99%. The selectivity with respect to pinacolone was 93%.

EXAMPLE 15

Preparation of pinacolone

A mixture of 15 g/h of pivalic acid, 52 g/h of acetic acid and 13 g/h of water was evaporated in an evaporator and passed, together with 3 l/h of nitrogen, at 400° C., over 100 ml of catalyst L, which contained 0.3 % by weight of sodium oxide, the remainder being anatase. The catalyst was prepared similarly to Example 1, by impregnating 997 g of $TiO_2$ carrier I with a solution which contained 3 g of $Na_2O$ (as aqueous NaOH). The reaction gases were then cooled and were collected in a receiver. From the discharged two-phase mixture, the organic and the aqueous phase were analyzed by gas chromatography. The conversion of pivalic acid was 97%. The selectivity with respect to pinacolone was 95%.

EXAMPLE 16

Preparation of pinacolone

A mixture of 9 g/h of pivalic acid, 32 g/h of acetone and 10 g/h of water was evaporated in an evaporator and passed, together with 3 l/h of nitrogen, at 410° C., over 100 ml of catalyst M, which contained 0.1% by weight of potassium oxide, the remainder being anatase. The catalyst was prepared similarly to Example 1, by impregnating 999 g of $TiO_2$ carrier II with a solution which contained 1 g of $K_2O$ (as aqueous KOH). The reaction gases were then cooled and were collected in a receiver. From the discharged two-phase mixture, the organic and the aqueous phase were analyzed by gas chromatography. The conversion of pivalic acid was 98%. The selectivity with respect to pinacolone was 90%.

EXAMPLE 17

Preparation of pinacolone

A mixture of 15 g/h of pivalic acid, 17 g/h of acetic acid, 17 g/h of acetone and 12 g/h of water was evaporated in an evaporator and passed, together with 3 l/h of nitrogen, at 430° C., over 100 ml of catalyst N, which contained 0.3% by weight of sodium oxide, the remainder being anatase. The catalyst was prepared similarly to Example 1, by impregnating 997 g of $TiO_2$ carrier II with a solution which contained 3 g of $Na_2O$ (as aqueous NaOH). The reaction gases were then cooled and were collected in a receiver. From the discharged two-phase mixture, the organic and the aqueous phase were analyzed by gas chromatography. The conversion of pivalic acid was 94%. The selectivity with respect to pinacolone was 96%.

We claim:

1. In a process for the preparation ketone of the formula

where $R^1$ and $R^2$ independently of one another are each alkyl of 1 to 17 carbon atoms, cycloalkyl having 3 to 8 ring members, arylalkyl, aryl or hetaryl, and one or more of the radicals $R^1$ and $R^2$ carry one or more hydrogen atoms on the α-carbon atom, by reacting two carboxylic acids of the formulae $R^1$—COOH (IIa) and $R^2$—COOH (IIb) or by reacting a carboxylic acid $R^1$—COOH (IIa) and $R^2$—COOH (IIb) or by reacting a carboxylic acid $R^1$—COOH (IIa) and a ketone

or by reacting a mixture of IIa, IIb and Ib, in the gas phase in the presence of a catalyst, the improvement which comprises:

carrying out the reaction with a catalyst in which the active material consists essentially of at least 50% by weight of titanium dioxide having a specific surface area greater than 10 m$^2$/g and from 0.05 to 50% by weight of one or more metal oxides from the first or second main group of the Periodic Table.

2. A process as claimed in claim 1, wherein titanium dioxide in the form of anatase is used.

3. A process as claimed in claim 1, wherein the catalyst contains from 0.05 to 50% by weight of lithium oxide, sodium oxide or potassium oxide.

4. A process as claimed in claim 1, wherein the catalyst has a specific surface area of from 20 to 200 m$^2$g.

5. A process as claimed in claim 1, wherein the catalyst has a specific surface area of from 30 to 160 m$^2$/g.

6. A process as claimed in claim 1, wherein the catalyst contains from 0.1 to 10% by weight of the oxide.

7. A process as claimed in claim 1, wherein R$^2$ is methyl and R$^1$ is tert-butyl.

8. A process as claimed in claim 1, wherein R$^1$ and R$^2$ are each ethyl.

9. A process as claimed in claim 1, wherein R$^2$ is methyl and R$^1$ is isopropyl.

10. A process as claimed in claim 1, wherein R$^2$ is phenyl and R$^1$ is ethyl.

11. A process as claimed in claim 1, wherein R$^2$ is phenyl and R$^1$ is cyclohexyl.

12. A process as claimed in claim 1, wherein R$^2$ is 3-pyridinyl and R$^1$ is methyl.

* * * * *

UNITED STATES PATENT AND TRADEMARK OFFICE
CERTIFICATE OF CORRECTION

PATENT NO. : 4,950,763
DATED : August 21, 1990
INVENTOR(S) : Schommer et al

It is certified that error appears in the above-identified patent and that said Letters Patent is hereby corrected as shown below:

In column 8 at line 46 of Claim 1: insert the words --of a-- between preparation and ketone.

Signed and Sealed this

Fifth Day of November, 1991

Attest:

HARRY F. MANBECK, JR.

Attesting Officer

Commissioner of Patents and Trademarks